US011904069B2

United States Patent
Wagner et al.

(10) Patent No.: US 11,904,069 B2
(45) Date of Patent: Feb. 20, 2024

(54) MG ALLOY MESH REINFORCED POLYMER/ECM HYBRID SCAFFOLDS FOR CRITICAL-SIZED BONE DEFECT REGENERATION

(71) Applicants: UNIVERSITY OF PITTSBURGH-OF THE COMMONWEALTH SYSTEM OF HIGHER EDUCATION, Pittsburgh, PA (US); UNIVERSITY OF CINCINNATI, Cincinnati, OH (US)

(72) Inventors: William R. Wagner, Gibsonia, PA (US); Sang-Ho Ye, Cheswick, PA (US); Yingqi Chen, Pittsburgh, PA (US); Vesselin Shanov, Cincinnati, OH (US)

(73) Assignees: UNIVERSITY OF PITTSBURGH-OF THE COMMONWEALTH SYSTEM OF HIGHER EDUCATION, Pittsburgh, PA (US); UNIVERSITY OF CINCINNATI, Cincinnati, OH (US)

( * ) Notice: Subject to any disclaimer, the term of this patent is extended or adjusted under 35 U.S.C. 154(b) by 714 days.

(21) Appl. No.: 16/498,035

(22) PCT Filed: Apr. 4, 2018

(86) PCT No.: PCT/US2018/025997
§ 371 (c)(1),
(2) Date: Sep. 26, 2019

(87) PCT Pub. No.: WO2018/187407
PCT Pub. Date: Oct. 11, 2018

(65) Prior Publication Data
US 2021/0187158 A1 Jun. 24, 2021

Related U.S. Application Data

(60) Provisional application No. 62/481,206, filed on Apr. 4, 2017.

(51) Int. Cl.
*A61L 27/04* (2006.01)
*A61L 27/34* (2006.01)
(Continued)

(52) U.S. Cl.
CPC ............ *A61L 27/047* (2013.01); *A61L 27/34* (2013.01); *A61L 27/3608* (2013.01);
(Continued)

(58) Field of Classification Search
CPC .... A61L 27/047; A61L 27/34; A61L 27/3608; A61L 27/3687; A61L 27/3691;
(Continued)

(56) References Cited

U.S. PATENT DOCUMENTS 7,208,222 B2 * 4/2007 Rolfe ...................... A61F 2/442
428/137
8,057,534 B2 * 11/2011 Boismier .............. A61L 31/148
623/1.46
(Continued)

FOREIGN PATENT DOCUMENTS

CA 2792081 A1 * 4/2013
CN 102327151 A * 1/2012
(Continued)

*Primary Examiner* — Brian A Dukert
*Assistant Examiner* — Melissa A Hoban
(74) *Attorney, Agent, or Firm* — Carol A. Marmo; Eckert Seamans Cherin & Mellott, LLC

(57) ABSTRACT

The invention relates to biomimetic, biodegradable composites including a magnesium (Mg) alloy mesh and a polymer/extracellular matrix (ECM). These hybrid composites, more particularly, are useful for the fabrication of medical implant devices, e.g., scaffolds, and are effective for bone regeneration. The fabrication process includes creating the Mg alloy mesh, and concurrently electrospinning the polymer and electrospraying the ECM onto the mesh.

3 Claims, 5 Drawing Sheets

(51) Int. Cl.
  *A61L 27/36* (2006.01)
  *A61L 27/44* (2006.01)
  *A61L 27/56* (2006.01)
  *A61L 27/58* (2006.01)

(52) U.S. Cl.
  CPC ....... *A61L 27/3687* (2013.01); *A61L 27/3691* (2013.01); *A61L 27/44* (2013.01); *A61L 27/56* (2013.01); *A61L 27/58* (2013.01); *A61L 2400/12* (2013.01); *A61L 2420/02* (2013.01); *A61L 2430/02* (2013.01)

(58) Field of Classification Search
  CPC .......... A61L 27/44; A61L 27/56; A61L 27/58; A61L 2400/12; A61L 2420/02; A61L 2430/02; A61L 27/427; A61L 27/48; A61L 27/54; A61F 2002/30971; A61F 2310/00041; A61F 2/2846; C22C 23/02; C22C 23/00
  See application file for complete search history.

(56) References Cited

U.S. PATENT DOCUMENTS

| | | | | |
|---|---|---|---|---|
| 8,815,275 | B2* | 8/2014 | Zhou | A61F 2/82 424/423 |
| 9,662,425 | B2* | 5/2017 | Lilja | C23C 4/134 |
| 10,709,816 | B2* | 7/2020 | Andersen | A61L 27/58 |
| 2003/0097170 | A1* | 5/2003 | Friedrich | A61F 2/07 623/1.13 |
| 2005/0038498 | A1* | 2/2005 | Dubrow | A61P 35/00 606/153 |
| 2005/0149175 | A1* | 7/2005 | Hunter | A61B 17/1219 623/1.42 |
| 2005/0221072 | A1* | 10/2005 | Dubrow | A61L 27/3821 428/292.1 |
| 2007/0179621 | A1* | 8/2007 | McClellan, III | A61F 2/442 264/241 |
| 2008/0033522 | A1* | 2/2008 | Grewe | A61L 31/082 623/1.11 |
| 2008/0265469 | A1* | 10/2008 | Li | D01D 5/0061 264/433 |
| 2009/0142505 | A1* | 6/2009 | Orr | B05B 5/087 427/458 |
| 2010/0049310 | A1* | 2/2010 | Quandt | C23C 30/00 623/1.46 |
| 2010/0057197 | A1* | 3/2010 | Weber | A61L 27/30 607/116 |
| 2011/0135806 | A1* | 6/2011 | Grewe | D01D 5/0076 427/2.25 |
| 2012/0209402 | A1* | 8/2012 | Ip | A61F 2/02 623/23.72 |
| 2013/0330688 | A1* | 12/2013 | Hedrick | A61C 8/00 606/228 |
| 2015/0105854 | A1* | 4/2015 | Shanov | A61L 31/16 216/9 |
| 2015/0297793 | A1* | 10/2015 | Mckay | A61L 27/54 424/549 |
| 2017/0014169 | A1* | 1/2017 | Dean | A61B 17/8071 |
| 2018/0044638 | A1* | 2/2018 | Bhattacharyya | A61F 2/4644 |
| 2018/0263751 | A1* | 9/2018 | Almasoud | A61L 15/44 |

FOREIGN PATENT DOCUMENTS

| | | | | |
|---|---|---|---|---|
| CN | 101558194 | B * | 12/2012 | .......... B01D 39/163 |
| CN | 106575750 | A * | 4/2017 | |
| WO | WO-2013166566 | A1 * | 11/2013 | |
| WO | WO-2015138034 | A2 * | 9/2015 | |
| WO | WO-2015138970 | A1 * | 9/2015 | ......... A61F 2/30756 |
| WO | WO-2017051650 | A1 * | 3/2017 | |
| WO | WO-2017179042 | A1 * | 10/2017 | |
| WO | WO-2019210059 | A9 * | 2/2020 | |

\* cited by examiner

MG ALLOY MESH REINFORCED POLYMER/ECM HYBRID SCAFFOLDS FOR CRITICAL-SIZED BONE DEFECT REGENERATION

CROSS-REFERENCE TO RELATED APPLICATIONS

This application is a U.S. National Stage Application under 35 U.S.C. §371 of PCT International Application No. PCT/US2018/025997, filed on Apr. 4, 2018, entitled "Mg Alloy Mesh Reinforced Polymer/ECM Hybrid Scaffolds For Critical-Sized Bone Defect Regeneration", which claims priority under 35 U.S.C. §119(e) to U.S. Provisional Patent Application Ser. No. 62/481,206, filed on Apr. 4, 2017, entitled "Mg Alloy Mesh Reinforced Polymer/ECM Hybrid Scaffolds For Critical-Sized Bone Defect Regeneration", which are herein incorporated by reference.

GOVERNMENT SUPPORT

This invention was made with government support under #EEC-0812348 awarded by the National Science Foundation (NSF). The government has certain rights in the invention.

FIELD OF THE INVENTION

The invention relates to biomimetic, biodegradable composites including a magnesium (Mg) alloy mesh and a polymer/extracellular matrix (ECM) material. These hybrid composites, more particularly, are useful for the fabrication of medical implant devices, e.g., scaffolds, and are effective for bone regeneration.

BACKGROUND

The repair of critical-sized bone defects remains a clinical challenge. In particular, for large-size bone defects that require replacement. Critical-sized bone defects, those that cannot be repaired without externally-derived factors, may result from trauma, primary tumors, congenital diseases and other causes. The repair of critical-sized calvarial defects remains challenging in terms of achieving adequate osteogenic regenerative efficacy as well as reaching suitable mechanical properties. Traditional approaches for bone regeneration include autologous bone grafting and the use of alloplastic implants. Both of these techniques, however, have disadvantages associated with their use. Autologous tissue is subject to limited availability, donor site morbidity, and infection risks. Allografts bring risks for immunoreactivity and the transmission of infectious agents.

Current strategies for the repair of calvarial defects are focused on construction of various scaffolds, including but not limited to:
  Porous ceramics including calcium phosphate, Mg phosphate, calcium silicate bioactive ceramics, and the like;
  Membranes including multilayered graphene hydrogel membranes, nanocomposite membranes, and the like;
  Hydrogels including nanosilver/nanosilica hydrogel, chitin nanofiber/calcium phosphate hydrogel, chitosan/hydroxyapatite hybrid hydrogel, poly(ethylene glycol) photopolymer-based hydrogels, and the like;
  Composites including chitosan-copper scaffolds, porous polymer/hydroxyapatite composites, with polymers including in-situ setting cross-linked polyurethanes and polyesters such as polyfumarate, and the like;
  Micro/nanofibrous scaffolds including hydroxyapatite/collagen/chitosan, mesoporous silica-layered biopolymer hybrids, polycaprolactone composite nanofibers, BMP-2 and dexamethasone loaded nanoparticle-embedded nanofibers, and the like; and
  Mg enhanced polymer systems including polylactic acid (PLA)-based composite reinforced with magnesium alloy wires, Mg alloy fiber reinforced poly(lactic-co-glycolic acid) (PLGA) composite, Mg wire reinforced phosphate cement composites, and the like.

Nanofibrous/Microfibrous scaffolds are readily fabricated using electrospinning technology, which is generally known in the art. The inherent nanofiber structure can provide connective porous network, which is beneficial for promoting bone cell adhesion, proliferation, migration, and nutrient transfer. Further, osteogenic differentiation can be induced from such scaffolds by adding bioactive particles or the controlled release of pharmacologic agents. It is preferred that biomaterials for bone regeneration exhibit the following properties: 1) biodegradability to avoid secondary surgeries, 2) suitable mechanical properties matched with surrounding tissue to reduce stress and strain imbalances, and 3) bioactivity to promote bone cell adhesion, proliferation, migration and the secretion of extracellular matrix (ECM) proteins. However, to date, research to address these problems simultaneously has been limited.

From a biologically-derived materials perspective, extracellular matrix (ECM) based materials, such as demineralized bone matrix (DBM), are relevant as a bone healing material, possessing a variety of bioactive factors, but lacking the mechanical properties needed in load bearing applications. DBM is generated from allograft bone that has been processed to remove most of the inorganic minerals, providing an organic collagen-rich matrix, including type I and some type IV and X collagens, growth factors (BMP2, BMP7) and other bioactive entities, which are known to facilitate osteoconduction and osteoinduction. As a support material, magnesium-based alloys have shown potential in bone repair applications in many pre-clinical, and more recently, clinical reports. The attractiveness of these alloy systems is based on several features. Most obviously, such alloys can be designed to experience oxidation and complete degradation in situ, avoiding secondary removal surgeries and their associated costs and morbidities. Further, the oxidative products from Mg alloy degradation are generally safe and common in bone. Indeed, the release of Mg ions can promote calcitonin gene-related polypeptide-α (CGRP) mediated osteogenic differentiation, which can be of therapeutic value. Furthermore, the mechanical properties of Mg alloys, particularly Young's modulus, can be similar to cortical bone, helping to minimize stress shielding that occurs with stiffer metallic implants. However, substantial advances must be made for Mg-based materials to be routinely used. The corrosion rate for many applications may be too rapid, leading to premature loss of mechanical properties and potentially the buildup of hydrogen gas pockets associated with the reduction reaction.

In considering the design features desirable for a device intended to facilitate calvarial defect regeneration, the following properties are considered most salient: 1) biodegradability to avoid secondary surgeries, 2) suitable mechanical properties, especially bending stress and bending modulus matched with surrounding tissue to reduce stress and strain imbalances, and 3) bioactivity to promote bone cell adhesion, proliferation, migration and secretion of extracellular matrix (ECM) proteins for subsequent calcification.

Thus, an object of the invention is to develop an effective hybrid scaffold for critical-sized bone defect regeneration, having mechanical properties that are enhanced over scaffolds produced by current technologies that utilize soft materials. A further object is to provide a biomimetic, biodegradable Mg alloy mesh-reinforced polymer/ECM (e.g., demineralized bone matrix (DBM)) hybrid scaffold fabricated by a concurrent electrospinning/electrospraying process. The Mg alloy mesh is for strength, form and bioactivity, DBM for broad bioactive component incorporation, and poly(lactic-co-glycolic acid) (PLGA) as a binding matrix for DBM. Yet another object is to design and develop a hybrid scaffold that exhibits one or more of enhanced osteoinductive, osteoconductive, osteogenic properties as compared to known implant materials.

SUMMARY OF THE INVENTION

In one aspect, the invention provides a biomimetic, biodegradable scaffold that includes a magnesium alloy mesh substrate and a composite applied to the substrate, wherein the composite includes electro-spun polymer fibers and electro-sprayed extracellular matrix.

The polymer fibers can include biodegradable polymer selected from a wide variety of such polymers that are known in the art. In certain embodiments, the polymer fibers include biodegradable polymer selected from the group consisting of polylactic acid, polyglycolic acid, polycaprolactone, poly(lactic-co-glycolic acid), poly(1,3-trimethylene carbonate), poly(ester urethane)urea, poly(carbonate urethane)urea and their derivatives, and mixtures thereof. The polymer fibers can be in a form selected from the group consisting of nanofibers, microfibers and mixtures thereof. The extracellular matrix can include demineralized bone matrix. The demineralized bone matrix can be selected from the group consisting of collagen, growth factor and mixtures thereof. The collagen can be selected from type I, type IV, type X and mixtures thereof. The growth factor can be BMP, such as BMP2 and BMP7.

In certain embodiments, the magnesium alloy mesh substrate includes a biodegradable metal.

In another aspect, the invention provides a method of fabricating a biomimetic, biodegradable composite. The method includes creating a magnesium alloy mesh, and concurrently electrospinning polymer and electrospraying extracellular matrix onto the magnesium alloy mesh.

The creating of the magnesium alloy mesh can include photochemical etching.

The method can further include embedding the magnesium alloy mesh into a polymer/extracellular matrix material.

In certain embodiments, the method includes rotating the magnesium alloy mesh on a mandrel during the electrospinning and electrospraying step.

The parameters of the electrospinning can be optimized to produce uniform electrospun polymer fibers. In certain embodiments, the magnesium alloy mesh is encapsulated with the electrospun polymer fibers and electrosprayed extracellular matrix.

The method can further include seeding bone marrow stem cells on a surface of the biodegradable composite and implanting the seeded, biodegradable composite into a patient body.

BRIEF DESCRIPTION OF THE DRAWINGS

A further understanding of the invention can be gained from the following description of the preferred embodiments when read in conjunction with the accompanying drawings in which.

DESCRIPTION OF THE PREFERRED EMBODIMENTS

Figure 1:
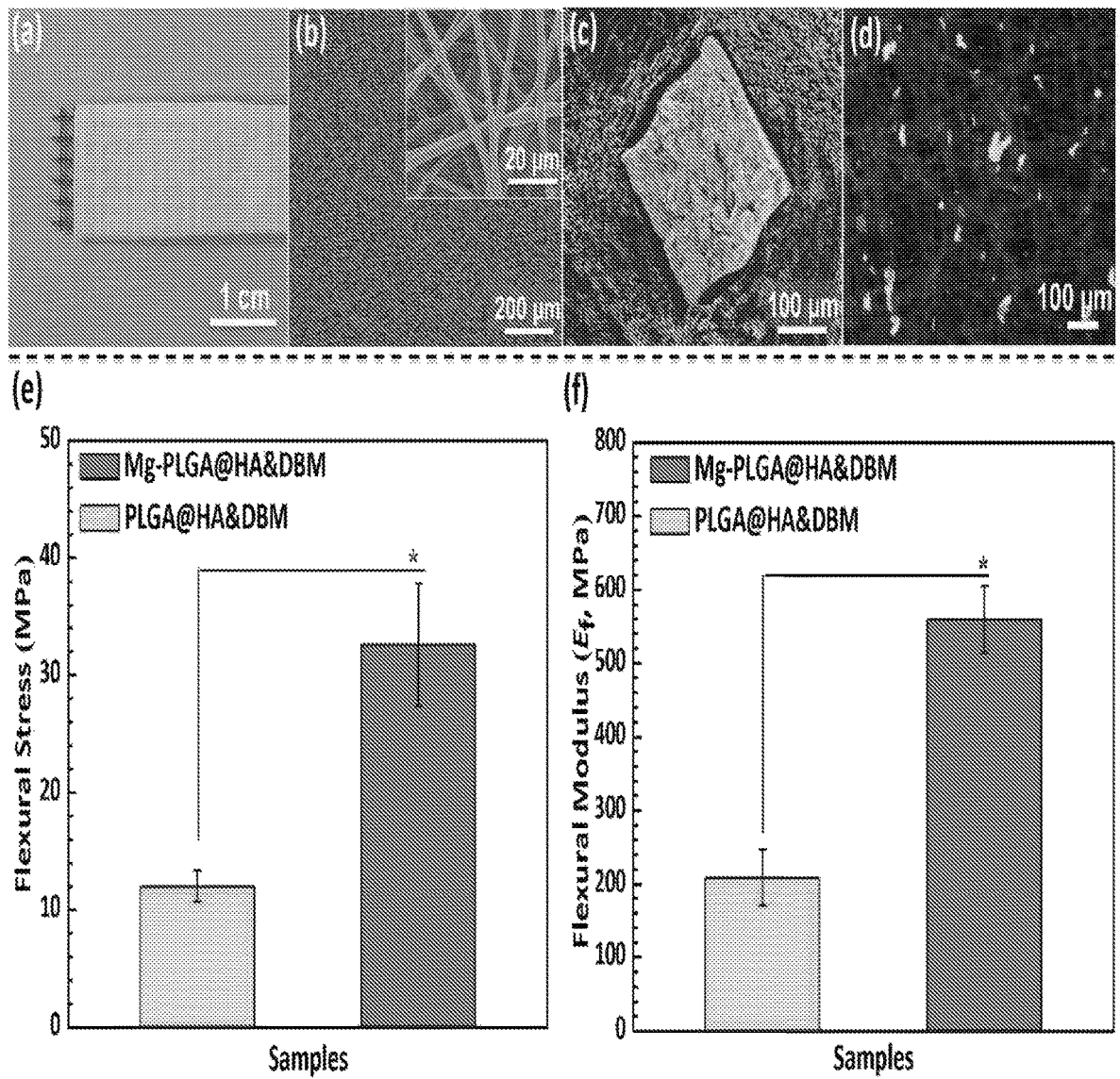
FIG. 1 is hybrid scaffold characterization of Mg mesh reinforced PLGA/DBM scaffold; view (a) is a macroscopic image of an as-fabricated scaffold, view (b) is a SEM image of PLGA electrospun fibers, view (c) is a cross-sectional morphology of the scaffold and view (d) is a fluorescent image of the Mg mesh reinforced PLGA/DBM scaffold, polymer solution labeled with fluoresceinisothiocyanate (FITC), and DBM particles stained by the (RHO) for identifying polymer fiber and DBM in the scaffolds, view (e) is a plot of the flexural stress and view (f) is a plot of the flexural modulus, in accordance with certain embodiments of the invention.

The invention relates to biomimetic, biodegradable composites that include a magnesium (Mg) alloy mesh and a polymer/extracellular matrix (ECM) composite. These hybrid composites are fabricated by concurrent electrospinning of the polymer and electrospraying of the ECM. The electrospun polymer/electrosprayed ECM composite is deposited onto the Mg alloy mesh. More particularly, these hybrid composites are useful for the fabrication of scaffolds, which are effective for bone regeneration. In certain embodiment, the hybrid composites are effective as biodegradable polymer/ECM hybrid scaffolds enhanced with a Mg mesh for calvarial critical-sized defects.

In certain embodiments, the hybrid scaffold is fabricated by concurrent electrospinning/electrospraying of a poly (lactic-co-glycolic acid) (PLGA) polymer and demineralized bone matrix (DBM) onto a Mg alloy mesh. The mechanical properties, including flexural stress and modulus, in vitro osteogenic differentiation capacity, and in vivo osteogenesis in a rat calvarial defect model are improved as compared to traditional materials.

The polymer component for use in the invention can be selected from a wide variety of suitable polymers known in the art. Non-limiting examples of suitable polymers include, but are not limited to, polylactic acid (PLA), polyglycolic acid (PGA), polycaprolactone (PCL), poly(lactic-co-glycolic acid) (PLGA), poly(1,3-trimethylene carbonate) (PTMC), poly(ester urethane)urea (PEUU), poly(carbonate urethane) urea (PCUU) and their derivatives, and mixtures thereof.

The ECM component can be selected from various suitable ECMs known in the art, such as, but not limited to, demineralized bone matrix (DBM). DBM consists of allograft bone wherein the inorganic mineral is removed therefrom. DBM provides an organic matrix, including collagen, growth factor, mixtures thereof and other bioactive entities. The collagen can be selected from type I, type IV, type X and mixtures thereof. The growth factor can be BMP, such as BMP2 and BMP7. The polymer and ECM components in the hybrid composites are effective to enhance osteoinductive, osteoconductive and osteogenic properties.

The Mg alloy mesh imparts bone-appropriate mechanical properties to the composites. The Mg alloy mesh can be composed of a suitable Mg alloy known in the art. Non-limiting examples of suitable Mg alloys include, but are not limited to, Mg-calcium (Ca), Mg-strontium (Sr), Mg-zinc (Zn), Mg-silicon (Si), Mg-aluminum (Al), Mg-rare earth and other biodegradable metals, and mixtures thereof. The Mg alloy mesh has similar modulus and density to natural cortical bone, which enhances the mechanical properties of the resulting composite, e.g., scaffold. The Mg alloy mesh releases Mg ions as it oxidizes, which provides an essential element that has been shown to stimulate bone regeneration. Specifically, recent studies have confirmed that Mg can promote calcitonin gene-related polypeptide-$\alpha$ (CGRP)-mediated osteogenic differentiation.

Fabrication of the composites include creating a Mg alloy mesh, blending a polymer, e.g., PLGA, with an ECM, e.g., DBM, and employing concurrent electrospinning/electrospraying to embed the Mg alloy mesh within a polymer/ECM, e.g., PLGA/DBM, hybrid composite. The polymer electrospun fibers can be in a form selected from nanofibers, microfibers and mixtures thereof. The polymer electrospun fibers can result in a porous, interconnected structure that is beneficial for subsequent bone cell adhesion and proliferation. In certain embodiments, the Mg alloy mesh is encapsulated by the electrospun polymer fibers/electrosprayed ECM composite. The ECM, e.g., DBM, can provide the organic collagen matrix, including the aforementioned type I and some types IV and X collagens, as well as growth factors (e.g., BMP2 and BMP7) to support osteoconduction and osteoinduction. This process and the resultant scaffold produced therefrom provide further support for bone cell adhesion, differentiation and proliferation.

In certain embodiments, a Mg alloy mesh, e.g., biodegradable metal substrate or foil, is created with the use of photochemical etching, which is a process that is amenable to a broad array of architectures. Generally, a photochemical etching process includes coating a metal substrate or metal sheet, for example, a Mg foil, with photosensitive resist, followed by photolithography to transfer a pattern on the Mg foil, and by chemical etching as a final step. The resulting etched Mg foil has a desired pattern that is determined by the photolithographic mask. An advantage of the described approach for manufacturing Mg meshes is that expensive laser cutting is avoided. The formation of the fine surface texture of the photo-chemically etched Mg mesh is a process that takes place at room temperature, and therefore no post-chemical etching or thermal annealing is needed. Also, the surface roughness of the photo-chemically etched Mg mesh depends on the surface roughness of the initial Mg foil used to make the Mg mesh. Photochemical etching prevents sputtering of Mg and re-deposition on the mesh surface, which can occur in typical laser cutting processes. Furthermore, photochemical etching is a scalable process, affordable in practice, and attractive for commercialization.

The Mg mesh is subjected to a concurrent electrospinning and electrospraying process. A polymer/ECM composite is deposited onto the Mg mesh by concurrent electrospinning of a polymer solution and electrospraying of an ECM solution. In certain embodiments, PLGA and DBM are selected as the polymer and ECM, respectively, for use in the concurrent electrospinning/electrospraying process. The polymer solution may include the polymer and hexafluoroisopropanol, and the ECM solution may include the ECM suspended in hyaluronic acid. In certain embodiments, the concurrent electrospinning/electrospraying process includes a rotating mandrel for the Mg alloy mesh such that the polymer/ECM composite is deposited onto, e.g., around, the mesh as it rotates.

A concurrent electrospinning/electrospraying process in accordance with the invention can include a DBM solution fed by a syringe pump into a capillary, which is suspended above a target mandrel with a Mg alloy mesh. Concurrently, a PLGA solution is fed from a capillary perpendicularly located from the target mandrel. The parameters of electrospinning the PLGA polymer can be optimized to obtain uniform electrospun fibers. The Mg alloy mesh mandrel can be rotated while translating back and forth along its rotational axis.

The surface and cross-section morphology of the resulting hybrid composite, e.g., scaffold, can be observed using various conventional techniques, such as, a scanning electron microscope (SEM). The mechanical property of the scaffold can be assessed by three-point bending test, tensile strength, compression testing and other suitable tests known in the art. Proliferation of bone marrow stem cells (BMSCs), as well as the osteogenic property (e.g., alkaline phosphatase activity (ALP) and calcium salt deposition), can be evaluated by seeding BMSCs on the surface of the scaffold. Further, an in-vivo test can be conducted by implanting the scaffold into a bone defect for a period of time (e.g., 4, 8 and 12 weeks). Furthermore, a micro-CT can be carried out to quantify the new bone formation.

In certain embodiments, the composition of the composite may be optimized. A mass ratio of Mg alloy mesh, polymer, e.g., PLGA, and ECM, e.g., DBM, can be optimized by the in-vitro BMSCs culture and the evaluation of osteogenic differentiation property. The mass ratio of Mg, PLGA and DBM may be 60:600:1, but is not limited to this ratio. Optimizing the composition of the composite provides the ability to tune or optimize the resulting mechanical properties exhibited by the composite.

The invention provides a composite that serves as an inductive scaffold for bone repair. The composite combines a bioactive ECM component from the DBM, Mg ions from the Mg alloy mesh, and a degradable polymer matrix for component support, integration and the potential for serving as a reservoir for controlled agent release. The combination of these components creates an architecture whereby a single composite is effective to simultaneously provide structural support elements, scaffolding, and the controlled release of inorganic and organic components that stimulate bone healing. Moreover, the invention provides a Mg alloy mesh-reinforced, polymer/ECM, e.g., PLGA/DBM, hybrid scaffold that possesses a highly porous and interconnected nano/micro fiber structure, which is fabricated by a concurrent electrospinning and electrospraying method.

A hybrid scaffold in accordance with certain embodiments of the invention includes a Mg alloy mesh, and a hybrid composite of electrospun PLGA nanofibers or microfibers and electrosprayed DBM deposited on, or applied to, the Mg alloy mesh. The PLGA/DBM composite can form a layer on one or more surface(s) of the Mg alloy mesh. The Mg alloy mesh can be embedded in the PLGA/DBM composite, or the PLGA/DBM composite can encapsulate the Mg alloy mesh. In certain embodiments, an upper layer and a lower layer of PLGA/DBM composite material are provided, wherein the Mg alloy mesh is positioned, e.g., "sandwiched", between the upper and lower layers of PLGA/DBM composite to form a stacked configuration. Optionally, a polymer, e.g., PLGA, layer or coating can be deposited onto, or applied to, one or more surfaces of the Mg alloy mesh prior to deposition, or application, of the PLGA/DBM composite such that the PLGA-coated Mg alloy mesh is embedded or encapsulated in the PLGA/DBM composite.

Without intending to be bound by any particular theory, it is believed that the alkaline corrosion products from the Mg structural components act to neutralize the acidic degradation products of PLGA, reducing the local inflammatory response commonly associated with scaffold material on surrounding tissues, e.g., when implanted in a body of a patient. Simultaneously, Mg ions stimulate pathways integral to bone tissue generation.

In accordance with the invention, a Mg alloy mesh reinforced polymer/demineralized bone matrix (DBM) hybrid scaffold is designed wherein the hybrid scaffold is fabricated by a concurrent electrospinning/electrospraying of poly(lactic-co-glycolic) (PLGA) polymer and DBM suspended in hyaluronic acid (HA). The Mg alloy mesh significantly increases the flexural strength and modulus of PLGA/DBM hybrid scaffold. In vitro results demonstrate that the Mg alloy mesh reinforced PLGA/DBM hybrid scaffold (Mg-PLGA@HA&DBM) exhibits a stronger ability to promote the proliferation of bone marrow stem cells (BMSCs) and induce BMSC osteogenic differentiation, as compared to scaffolding materials lacking the novel components. In vivo osteogenesis studies performed in a rat critical-sized calvarial defect model and incorporated a variety of histological stains and immunohistochemical staining of osteocalcin, at 12 weeks, showed that the degree of bone repair for the Mg-PLGA@HA&DBM scaffold is significantly greater than for those scaffolds lacking one or more of the novel components. The improved mechanical properties, promotion of BMSC proliferation and induction of BMSC osteogenic differentiation, and improved promotion of bone repair in the rat critical-sized calvarial defect model, make Mg alloy mesh reinforced PLGA/DBM hybrid scaffold suitable for the repair of critical-sized bone defects where the addition of exogenous isolated growth factors is not employed.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims appended and any and all equivalents thereof.

EXAMPLES

A hybrid scaffold in accordance with the invention was prepared and evaluated in accordance with the following objectives: 1) construct and optimize a PLGA/DBM hybrid scaffold with Mg alloy mesh using a concurrent electrospinning/electrospraying technique; 2) investigate the characteristics of the hybrid scaffold (e.g., surface morphology and cross-sectional SEM images) and the mechanical properties; 3) perform in-vitro bone marrow stem cell study to confirm the in-vitro osteogenic induction property of the hybrid scaffold; and 4) verify the feasibility of the hybrid scaffold with an in-vivo model for calvarial defect repair.

A concurrent electrospinning/electrospraying method was used to fabricate a Mg alloy mesh enhanced PLGA/DBM hybrid composite scaffold. A solution of 5 mg/mL DBM with sodium hyaluronate (2 mg/mL DI water) at a temperature of 4° C. was prepared and fed by a syringe pump into a capillary (1.2 mm I.D.), suspended above a target rotating plate with a Mg alloy mesh mandrel (the width of plate was 40 mm). Concurrently, PLGA (MW-150,000Da, PolySciTech, USA) in hexafluoroisopropanol (HFIP, US) solution (20%, w/v) was fed from a capillary, perpendicularly located from the target mandrel. The mandrel was rotated at 50 rpm while translating back and forth 6 cm along its rotational axis at 0.3 cm/s.

The surface and cross-section morphology of the resulting Mg alloy mesh enhanced PLGA/DBM hybrid composite scaffold was observed using a scanning electron microscope (SEM). Tensile strength and compression testing was conducted to evaluate the mechanical property of the scaffold. The proliferation of bone marrow stems cells (BMSCs), as well as the osteogenic property (e.g., alkaline phosphatase activity (ALP) and calcium salt deposition), were evaluated after seeding the BMSCs on the scaffold surface for 7, 14 and 21 days. Further, a preliminary in-vivo use was also investigated with a calvarial defect animal (rat) model. The scaffold was implanted into the calvarial defect and after 4, 8 and 12 weeks, a micro-CT was performed to quantify the new bone formation during each of these time periods. Gene expression analysis of angiogenesis-related PCR was performed. Hematoxylin/eosin (H&E) staining, Masson's trichrome staining and immunohistochemical staining (osteocalcin, OCN) was then selectively performed.

The parameters of electrospinning the PLGA polymer were optimized to obtain uniform electrospun PLGA fibers. Surface morphology and cross-sectional SEM images of the hybrid scaffold were the first data obtained. The appropriate mass ratio of Mg alloy mesh, PLGA and DBM in the sample was optimized by the in-vitro BMSCs culture and the evaluation of osteogenic differentiation property. After optimizing the composition of the hybrid scaffold, and with promising results of the in-vitro study, a primary in-vivo calvarial defect animal study was performed.

Example 1

A Mg alloy mesh was created with photochemical etching in a process amenable to a broad array of architectures. A polymer/ECM composite was deposited onto the mesh by concurrent electrospinning of a solution of PLGA polymer and electrospraying a solution of DBM. This hybrid scaffold was characterized in terms of physical properties (morphology and mechanical properties), as well as osteogenic properties in-vitro, and compared to scaffolds lacking one or more of the components.

Method:

A Mg alloy mesh was fabricated by photochemical etching an AZ31 alloy foil (250 µm thick). The composition of AZ31 is 2.5-3.5 wt % for Al, 0.7-1.3 wt % for Zn, 0.2 wt % (min) for Mn, 0.05 wt % (max) for Si, 0.05 wt % (max) for Cu, 0.04 wt % (max) for Ca, 0.005 wt % (max) for Fe, 0.005 wt % (max) for Ni, 0.30 wt % (max) for others and a balance of Mg. Concurrent electrospinning/electrospraying was used to embed the Mg alloy mesh within a PLGA/DBM hybrid composite scaffold. DBM powder (5 mg/mL) with sodium hyaluronate (HA) (2 mg/mL DI water) solution was fed by a syringe pump into a positively charged capillary suspended above a rotating plate holding the Mg alloy mesh mandrel. Concurrently, PLGA (~150 KDa) in hexafluoroisopropanol solution (20%, w/v) was fed from a capillary located perpendicular to the target mesh mandrel. The mesh mandrel was rotated while translating back and forth 6 cm along its rotational axis. The cross-section scaffold morphology was imaged with electron microscopy (SEM). The osteogenic properties (e.g., alkaline phosphatase activity and calcium deposition) were evaluated following seeding of bone marrow stem cells (BMSCs) on the scaffold for 7, 14 and 21 days.

Results:

For the Mg alloy mesh embedded within the PLGA/DBM scaffold as fabricated using the concurrent electrospinning/electrospraying method, a cross-sectional image demonstrated the encapsulation of the Mg alloy mesh by the PLGA polymer fibers.

The hybrid scaffold exhibited a similar bone marrow stem cell proliferation rate as compared to TCPS and a composite without Mg alloy mesh in a 7-day culture. Alizarin red staining results of BMSC seeding on various sample surfaces for a period of 21 days showed that PLGA@HA&DBM and Mg-PLGA@HA&DBM samples presented statistically more red color generation as compared to the other surfaces, confirming greater osteogenic differentiation of these samples. Also, Mg-PLGA@HA&DBM significantly exceeded PLGA@HA&DBM in this parameter, indicating a further effect attributable to the presence of the Mg alloy mesh.

Conclusions:

The novel bio-hybrid scaffold, generated by embedding a Mg alloy mesh within a polyester nanofiber/DBM composite was successfully fabricated by employing a concurrent electrospinning/electrospraying technique. The Mg alloy/polymer nanofiber/ECM hybrid scaffold (Mg-PLGA@HA&DBM) demonstrated osteogenic activity in-vitro that was most differentiated as compared to scaffolds lacking in one or more components.

Example 2

A rectangular sheet (200×500 mm, 250 µm thick) of AZ31 magnesium alloy was purchased from Goodfellow USA. According to the vendor, the alloy composition was: 3% Al, 1% Zn, with the balance Mg. Using a methodology previously described (Shanov et al., 2017) photo-lithographically was utilized to transfer a mesh pattern (with square-shaped pores of 1.5×1.5 mm) onto AZ31 foil, followed by chemical etching.

Fabrication of Mg Mesh Reinforced PLGA/DBM Hybrid Scaffold:

A concurrent electrospinning/electrospray method was used to fabricate the Mg alloy mesh reinforced PLGA/DBM hybrid composite scaffold. PLGA (85:15 LA:GA, MW~150,000 Da, PolySciTech, USA) in hexafluoroisopropanol (HFIP, Sigma-Aldrich, US) solution (20%, w/v) was fed at 1.5 mL/hr from a capillary perpendicularly located from a rotating stainless steel flat target. The target was comprised of two identical plates atop one another that each incorporated a cut out (60×40 mm). The Mg mesh (65×10 mm) was placed centrally in between the two plates to secure it in the center of the open gap area (with 15 mm open gap on each side). The voltage of the target and PLGA solution capillary was −6 kV and +8 Kv, respectively. The distance between the central axis of target and the polymer infusing capillary was 170 mm. The target was rotated at 50 rpm while translating back and forth over a 6 cm distance along the rotational axis at 0.3 cm/s. After 2 hr deposition time, PLGA fibers encased the entire Mg mesh and the formerly open gap regions on each side of the mesh. At that time, the process was altered. DBM (Canine Demineralized Bone Matrix, Veterinary Transplant Services, Inc, USA) powder suspended at 5 mg/mL in sodium hyaluronate solution (HA700K-5, Lifecore Biomedical, USA, 2 mg/mL DI water) at 4° C. was fed by a syringe pump into a capillary (1.2 mm I.D.) with an infusion rate of 2 mL/hr. The capillary was suspended above the rotating Mg mesh target and perpendicular to the capillary delivering the PLGA solution. The distance between the central axis of the target and the DBM infusing capillary was 70 mm. After 5 hr of concurrent electrospinning of PLGA and electrospraying of the DBM solution, the PLGA/DBM hybrid scaffold was obtained. The rectangular gap in the two target plates was comprised of three sections. The central section was the Mg alloy mesh encased in the PLGA/DBM composite, while the flanking sections had deposited PLGA and PLGA/DBM, but lacked the Mg alloy mesh. The three sections were separated by cutting lengthwise. After freeze drying, the samples were stored at −20° C. until further characterization.

Hybrid Scaffold Characterization:

Macroscopic images were taken by digital camera. The surface morphology and cross-sectional images of the Mg mesh encapsulated in PLGA/DBM were observed with scanning electronic microscopy (SEM, JEOL 6330F) after gold sputtering. For cross-section preparation, the scaffold was frozen and broken in liquid nitrogen. Fluorescent images of the PLGA/DBM scaffold were taken for scaffolds where the polymer solution was labeled with fluorescein isothiocyanate (FITC), and the DBM particles were stained by rhodamine (RHO) to clearly identify each component in the scaffold.

Flexural Strength Measurement:

Three-point bending tests were conducted to measure the flexural strength and flexural modulus of the hybrid scaffolds with and without Mg mesh. The measurements were performed in a bending test device (ElectroForce 3200 (Bose, Minn.)) according to a standard testing protocol. Specifically, the Mg mesh with PLGA/DBM scaffold (15×10×1 mm) and PLGA/DBM scaffold (15×10×0.7 mm) were placed on two supporting pins at a set distance of 12 mm, and then bent under loading yield occurred.

The flexural stress ($\sigma_f$) and flexural modulus ($E_f$) were obtained according to equations (1) and (2):

$$\sigma f = \frac{3FL}{2bd^2} \quad (1)$$

$$Ef = \frac{L^3 m}{4bd^3} \quad (2)$$

wherein, σf stands for the flexural stress (MPa); F is the load at a given point on the load deflection curve (N); L, b and d represent support span (mm), width of test beam (mm) and depth or thickness of tested beam (mm), respectively; m is related to the slope of the initial straight-line portion of the load deflection curve (N/mm).

Rat Bone Mesenchymal Stem Cell (BMSC) Culture Study:

Rat bone mesenchymal stem cells (BMSCs, OriCell Fisher 344 (F344), Cyagen, USA) were cultured in OriCell MSC Growth Medium (Cyagen, USA) in a humidified incubator under 5% CO2 at 37±0.5° C. Then, the BMSCs (under an original passage number of 10) were digested by trypsin, and the cells were seeded on the scaffold (10 mm diameter, punched from the original scaffolds) at a density of 2×10⁴ cells/mL. After 3 hr incubation to allow cell attachment, the samples were transferred into a new 24 well plate for further culture. Tissue culture polystyrene (TCPS) discs of the same size as the samples were similarly seeded with cells and cultured with OriCell MSC Growth Medium or Osteogenic Differentiation Basal Medium (GUXMX-03021-175, Cyagen, USA) respectively, to serve as negative and positive controls. The proliferation of BMSCs on the scaffolds was assessed using an MTS assay kit (Promega CellTiter 96 Cell Proliferation Assay, n=4). After 1, 3 and 7 days culture, the samples were carefully transferred into a new 24-well plate, and then 0.5 mL cell culture medium mixed with MTS reagent (9:1) was added. After 3 hr incubation, 150 μL of the medium was carefully transferred to a 96-well. The optical density was measured at 490 nm using a microplate reader. For SEM observations of cells adhered on the scaffolds, after 7 days culture the scaffolds were washed with pre-warmed PBS three times. Then the cells on the scaffolds were fixed with 2.5% glutaraldehyde. After that, the cells were subjected to dehydration in graded series of alcohol/DI water solutions (30%, 50%, 70%, 90% and 100%) for 15 min each. The samples were then immersed in hexamethyldisilazane (HMDS) for 5 min. Finally, the scaffolds with cells were gold-sputtered prior to SEM observation.

Alkaline phosphatase (ALP), as an early osteogenic differentiation marker, is a hydrolase enzyme responsible for removing phosphate groups from many types of molecules. After 7 and 14 days culture, the samples were washed with PBS three times and the cells on the sample surface were lysed with 0.2 mL 1% (v/v) Triton X-100 for 12 hr at 4° C. Then the cell lysate solution was centrifuged and the supernatant was used for ALP activity assessment. The total protein concentration of the cell lysate for each sample was measured using the bicinchoninic acid (BCA, Sigma-Aldrich, USA) protein assay kit. The final ALP activity was normalized with respect to the total protein content obtained from the same cell lysate. The number of independent samples used for statistics was no less than four and all of the assays were repeated more than two times.

For calcium deposition assessment, after 21 days of BMSC culture the samples were carefully transferred into a new 24-well plate and washed with pre-warmed PBS three times. Alizarin red solution (1 mL of 2%; Sigma-Aldrich, USA) was slowly added to each well, and then incubated for 20 min at room temperature. After that, the excess dye was removed from each well and washed several times with DI water until no further removal was observed, as verified by comparison of optical densities using a microplate reader of the DI water used as a wash with pristine DI water. Samples were then imaged macroscopically. For quantification of alizarin red staining, the samples were treated with 150 μL 10 wt % hexadecylpyridinium chloride (Sigma-Aldrich, USA)/PBS solution to solubilize the dye, followed by measurement of absorbance at 570 nm with a microplate reader.

In Vivo Animal Study and Surgical Procedures:

Female Sprague-Dawley rats (SD rats, 150-170 g) were purchased from Harlan Sprague Dawley Inc. USA. The rats were randomly divided into five groups (n=5 each group). After anesthetization with 10% chloral hydrate (4 mL/kg), the rats were shaved on the head, and the epicranium was cut longitudinally. The critical-sized calvarial defect (8 mm diameter) was made using a dental drill. The scaffold samples were cut in a disc (8 mm diameter) using a punch. The disc samples were then physically placed in the defect and the wound was carefully sutured. After 12 weeks implantation, the rats were anesthetized with 10% chloral hydrate (4 mL/kg), and 3D computed tomography data of the rat calvaria were obtained with a Vivo 40 micro-CT system (Scanco, Switzerland).

Histological Assessment and Immunohistochemical Staining:

After a 12 weeks-implant period, the rats were anesthetized and sacrificed. The whole calvaria was removed and fixed in 4% paraformaldehyde solution for 1 wk. The harvested calvaria were dehydrated with an increasing series of ethanol baths (70%, 75%, 80%, 85%, 90%, 95%, and 100%) for 24 hr each, and were then embedded in paraffin. The cross section of the central area of the defects were cut (5 μm thick) for further histological evaluation. Hematoxylin/eosin (H&E) and Masson's trichrome staining were performed on isolated sections, as was Von Kossa staining to confirm the presence of calcified tissue (Von Kossa kit, Abcam, USA).

Immunohistochemical staining of osteocalcin (OCN) was investigated to examine osteogenesis. Sections of explanted tissue were deparaffinized by dipping in xylene three times (3 min for each), followed by 100%, 95%, and 70% ethanol washes for 1 min each, and running water for 2 min respectively. Subsequently, the sections were immersed in an antigen retrieval buffer (HistoVT One, Nacalai Tesque, INC. Japan) at 95-100° C. for 20 min to expose the antigen on the surface. After the buffer solution was cooled to room temperature, the sections were washed with PBS three times (3 min for each), and then incubated in blocking solution (2% normal horse serum, 1% BSA, 0.1% Triton X-100 and 0.1% Tween-20 in 1× PBS, pH 7.4) in a humidified chamber for 1 h at room temperature to inhibit non-specific binding. After removing the blocking solution, the primary antibody of OCN (Osteocalcin antibody, orb259644, Biobyt, USA) diluted in blocking solution (2.5 μg/mL (1:200)) was added to cover the sections and incubated in a humidified chamber at 4° C. overnight. After removing the primary antibody, the slices were washed with PBS three times (3 min for each). The fluorescently-labeled secondary antibody (donkey anti-rabbit, ab150073, Abcam, USA) diluted in blocking solution (1:450) was added to the sections and incubated in a humidified chamber at room temperature in the dark for 1 hr. After removing the secondary antibody, the slices were washed with PBS three times (3 min for each). Finally, nuclei were stained with 4′,6-diamidino-2-phenylindole (DAPI; 1:10000, Sigma, USA). For each sample, more than 5 different microscopic images were taken under fluorescence microscopy to view OCN positive structures.

Statistical Analyses:

All the data are expressed as mean±standard deviation (as error bars in the figures) determined from at least four independent experiments. The statistical analyses performed to evaluate differences were one-way analysis of variance (one-way ANOVA), with post hoc Newman-Keuls testing, where a p value of less than 0.05 was considered to be statistically significant.

Results

Morphology and Mechanics of Mg Mesh Reinforced PLGA/DBM Hybrid Scaffold:

FIG. 1, views (a)-(d), shows the formed composite material of the Mg mesh integrated within the polymer/extracellular matrix (PLGA/DBM) hybrid material from macroscopic and microscopic perspectives. The surface of deposited PLGA fibers had a fiber diameter of 3±0.5 and scaffold cross-sections showed encapsulation of the Mg mesh by polymer fibers. In FIG. 1(d), distinct regions of DBM were seen to be distributed amongst the PLGA fibers.

The flexural strength and modulus of the PLGA/DBM hybrid scaffolds with and without Mg mesh as examined by three-point bending are shown in FIGS. 1(e) and 1(f). The Mg mesh strengthened and stiffened the polymer/extracellular matrix hybrid scaffold.

Figure 2:
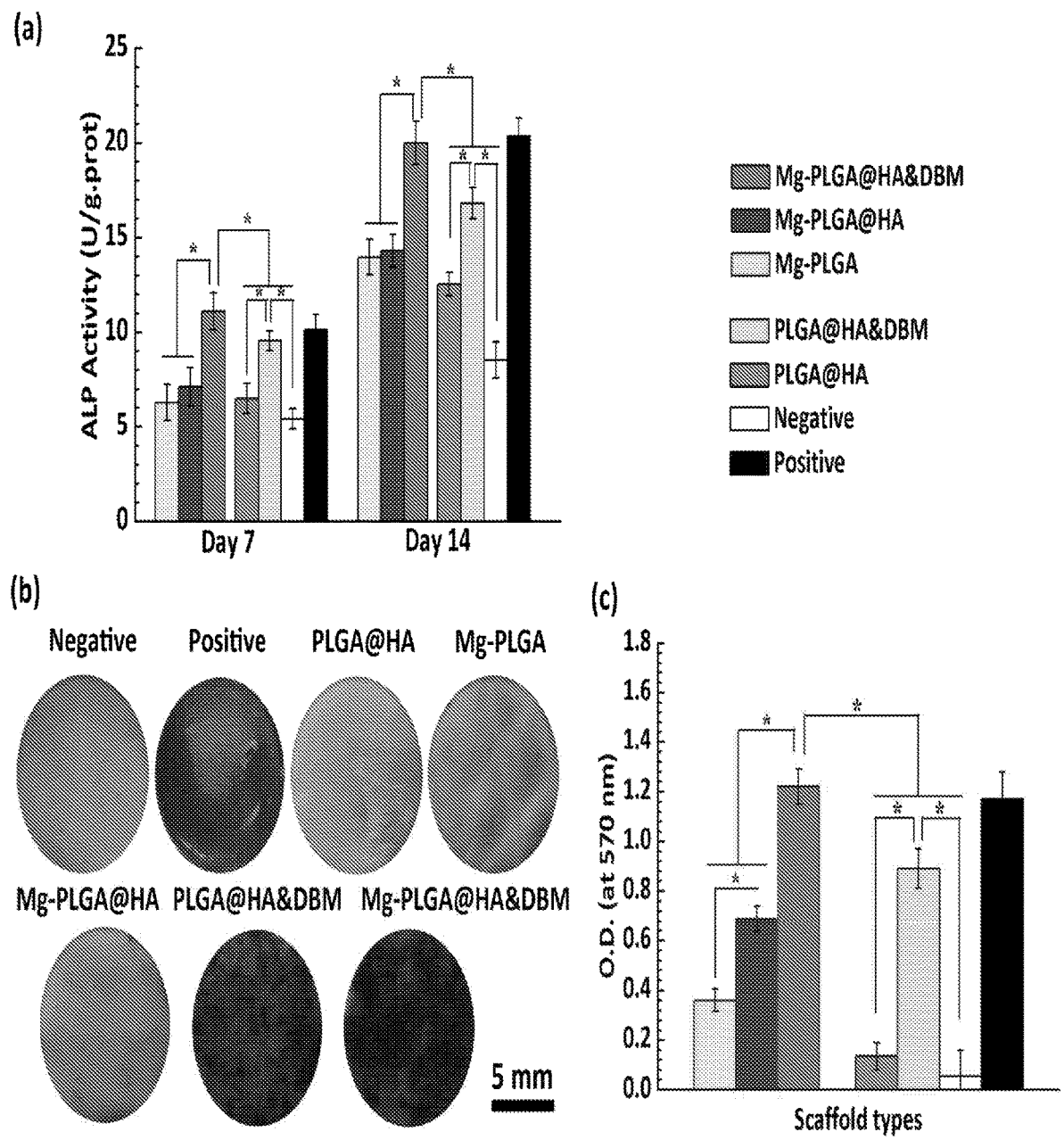
FIG. 2 shows view (a) which is a plot of alkaline phosphatase (ALP) activity results of the scaffolds after 7 and 14 days of BMSC culture; view (b) which shows images of alizarin red staining; and view (c) which is a plot of alizarin red quantity after BMSC seeded on scaffolds for 21 days, in accordance with certain embodiments of the invention.

In Vitro ALP Activity and Calcium Deposition:

FIG. 2(a) demonstrates increasing ALP activity with culture time for BMSCs cultured on the various scaffolds. The ALP activity on PLGA/DBM hybrid scaffold (PLGA@HA&DBM) was higher than that for the scaffold without DBM (PLGA@HA), and this activity was further increased when the Mg mesh was included (Mg-PLGA@HA&DBM) at 7 and 14 days of culture. Alizarin red staining is shown qualitatively and quantitatively in FIGS. 2(b) and 2(c) for BMSCs cultured on scaffolds for 21 days. Measurements of optical density of the dissolved alizarin red that had bound to the cultured surfaces was greater for PLGA@HA@DBM and Mg-PLGA@HA&DBM, consistent with greater calcium deposition. Furthermore, Mg-PLGA@HA&DBM had greater alizarin red binding than PLGA@HA&DBM, indicating an effect attributable to the presence of the Mg mesh.

In Vivo Animal Study

Figure 3:
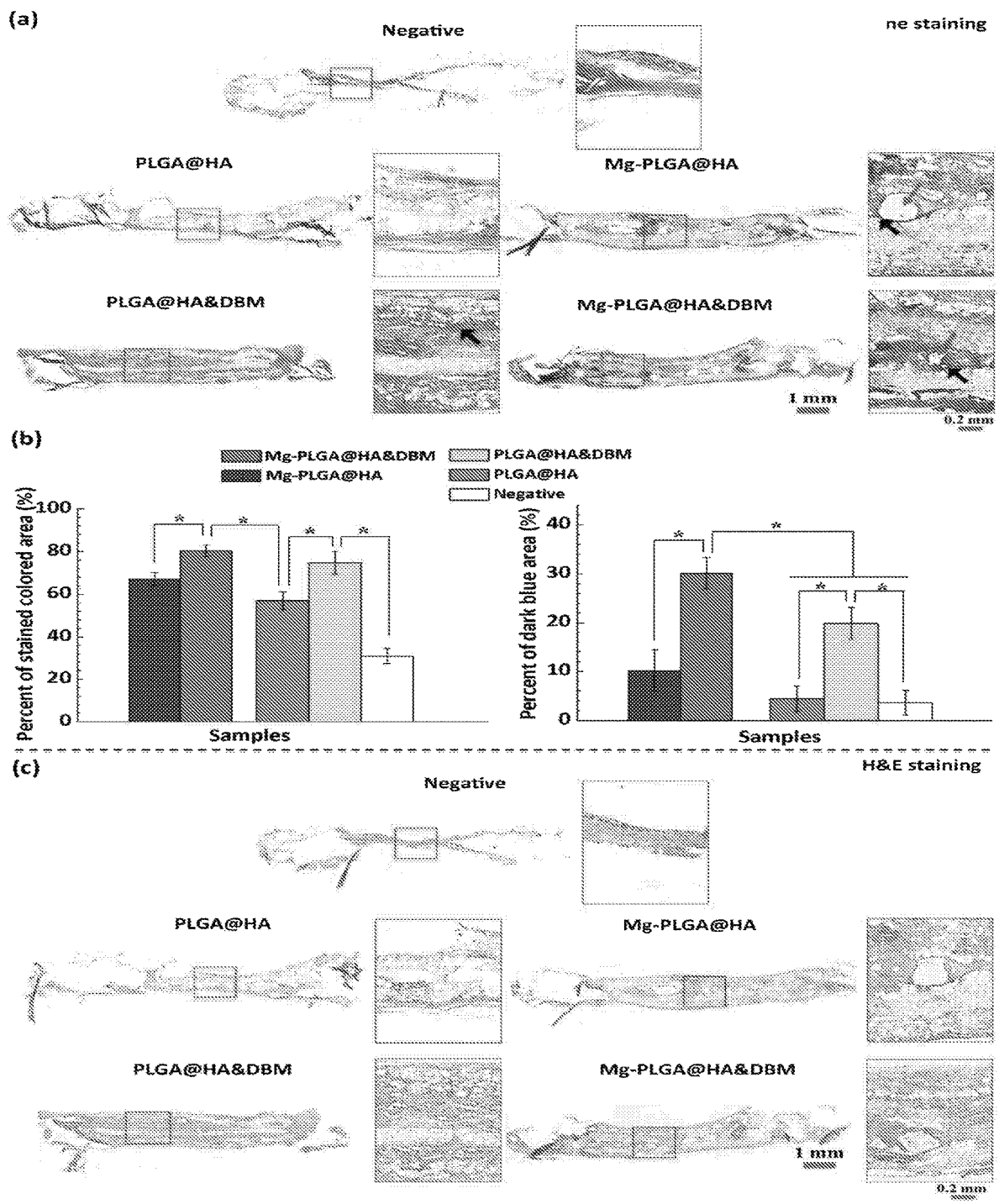
FIG. 3 shows view (a) which are images of Masson trichrome staining of scaffolds after implantation for 12 weeks; view (b) which are plots of the quantification for stained colored area of Mg-PLGA@HA&DBM, PLGA@HA&DBM, Mg-PLGA@HA, PLGA@HA and Negative groups after 12 weeks of implantation in critical sized calvarial defect; and view (c) which are images of H&E staining of Mg-PLGA@HA&DBM, PLGA@HA&DBM, Mg-PLGA@HA, PLGA@HA scaffolds and Negative controls after implanted for 12 weeks, in accordance with certain embodiments of the invention, and comparison scaffolds.

Masson Trichrome Staining and Hematoxylin and Eosin (H&E) Staining:

The in vivo osteogenic properties of the scaffolds were investigated in a critical-sized calvarial defect for 12 wk. In FIGS. 3(a) and 3(b), representative Masson trichrome stained sections are presented together with quantitative image analysis of all stained areas and blue stained areas measured from trichrome stained sections from scaffolds after 12 wk implantation. The staining patterns in Mg-PLGA@HA&DBM and PLGA@HA&DBM showed more general staining as well as more blue stained areas compared to the other scaffold types. Also, the Mg-PLGA@HA&DBM displayed more blue stained areas compared to PLGA@HA&DBM. There was also more general and blue staining observed on Mg-PLGA@HA scaffolds than PLGA@HA scaffolds. Blue staining was obvious and consistently present in the regions surrounding what appeared to be voids left behind by the Mg struts. The negative control group, where no implant was made, presented a very thin tissue covering over the defect.

H&E staining and analysis of recovered tissue sections from the defect site are presented in FIG. 3(c). Consistent with the Masson trichrome staining results, more staining was present on Mg-PLGA@HA&DBM and PLGA@HA&DBM scaffolds compared to the others, and Mg-PLGA@HA scaffold displayed more stained area than that of the PLGA@HA scaffold. The negative control revealed minimal staining. Mg-PLGA@HA&DBM and Mg-PLGA@HA scaffolds presented some regions noticeable around Mg struts that had a staining and morphology consistent with new forming bone.

Von Kossa Staining:

With Von Kossa staining (FIG. 4) regions stained black that would be consistent with phosphate deposits, including calcium phosphate and magnesium phosphate, were quantified. No such staining was found in the negative control sections, with staining only present in the peripheral bony regions of the defect. PLGA@HA displayed very sparse stained areas that increased modestly with the presence of the Mg mesh. A noticeable increase in staining was present with the PLGA@HA&DBM scaffold versus the Mg-PLGA@HA, despite the lack of Mg, while the strongest staining was when both DBM and Mg were present in the Mg-PLGA@HA&DBM. The quantitative results in FIG. 4b confirmed these observations.

Figure 5:
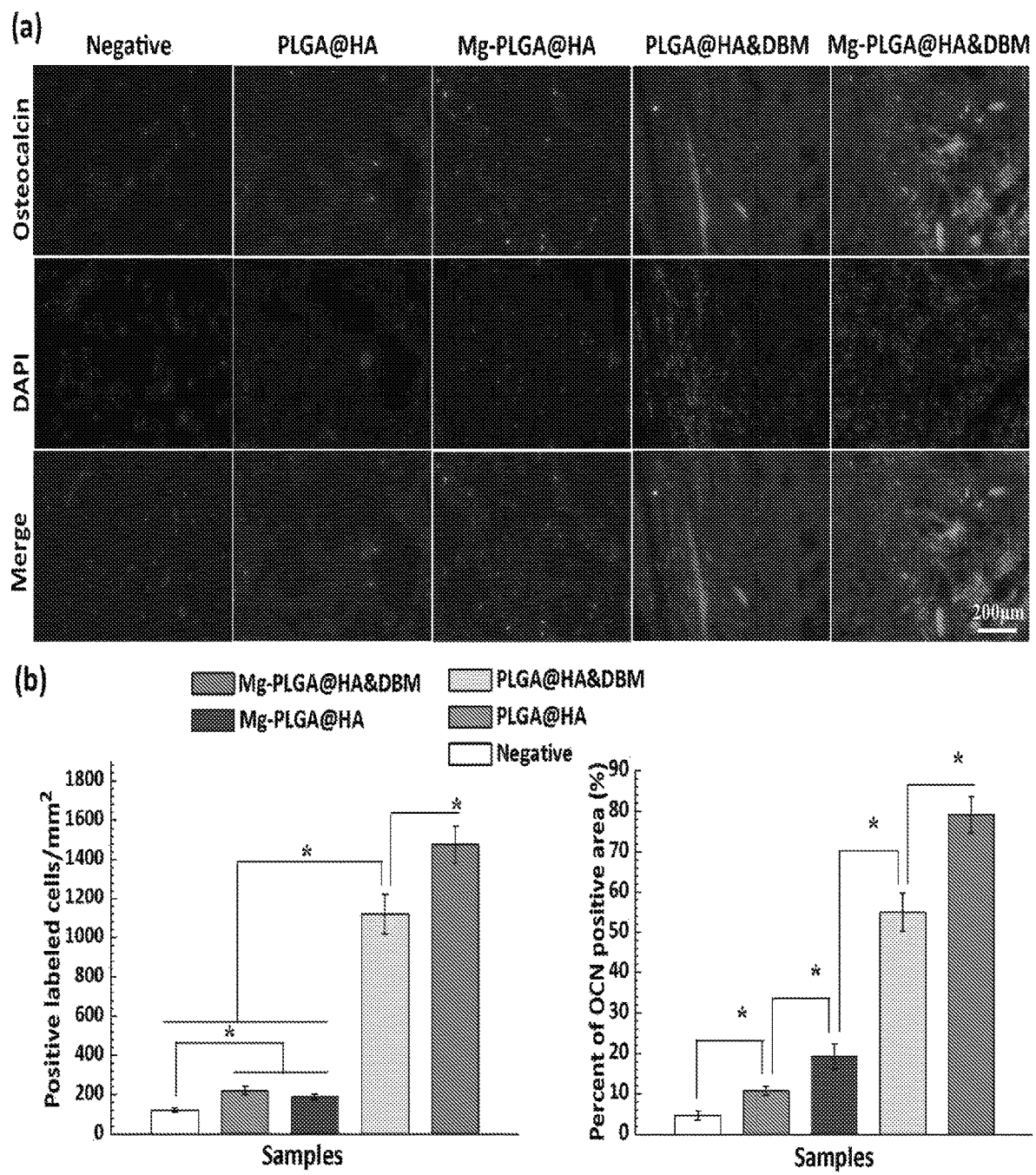
FIG. 5 shows view (a) which are images of immunohistochemical staining of the osteogenic marker of scaffolds after implantation in a critical-sized calvarial defect for 12 weeks; and view (b) which are plots of the quantification for bone-related cell numbers and OCN protein expression area of Mg-PLGA@HA&DBM, PLGA@HA&DBM, Mg-PLGA@HA, PLGA@HA implanted in a critical-sized calvarial defect for 12 weeks as compared to Negative controls, in accordance with certain embodiments of the invention.

Immunohistochemical Staining:

Immunohistochemical staining was examined to further assess osteocalcin (OCN) expression in the implanted scaffolds after 12 wk. Immunohistochemical OCN staining and quantification of positively labeled cell number and area of labeling are shown in FIG. 5. The quantitative results showed that Mg-PLGA@HA&DBM scaffold presented both a larger number of positively stained cells and a greater area of OCN-positive staining than all of the other scaffold types and the negative control. Both the addition of Mg and the addition of DBM increased the OCN stained area versus the scaffolds lacking these components.

Discussion

Figure 4:
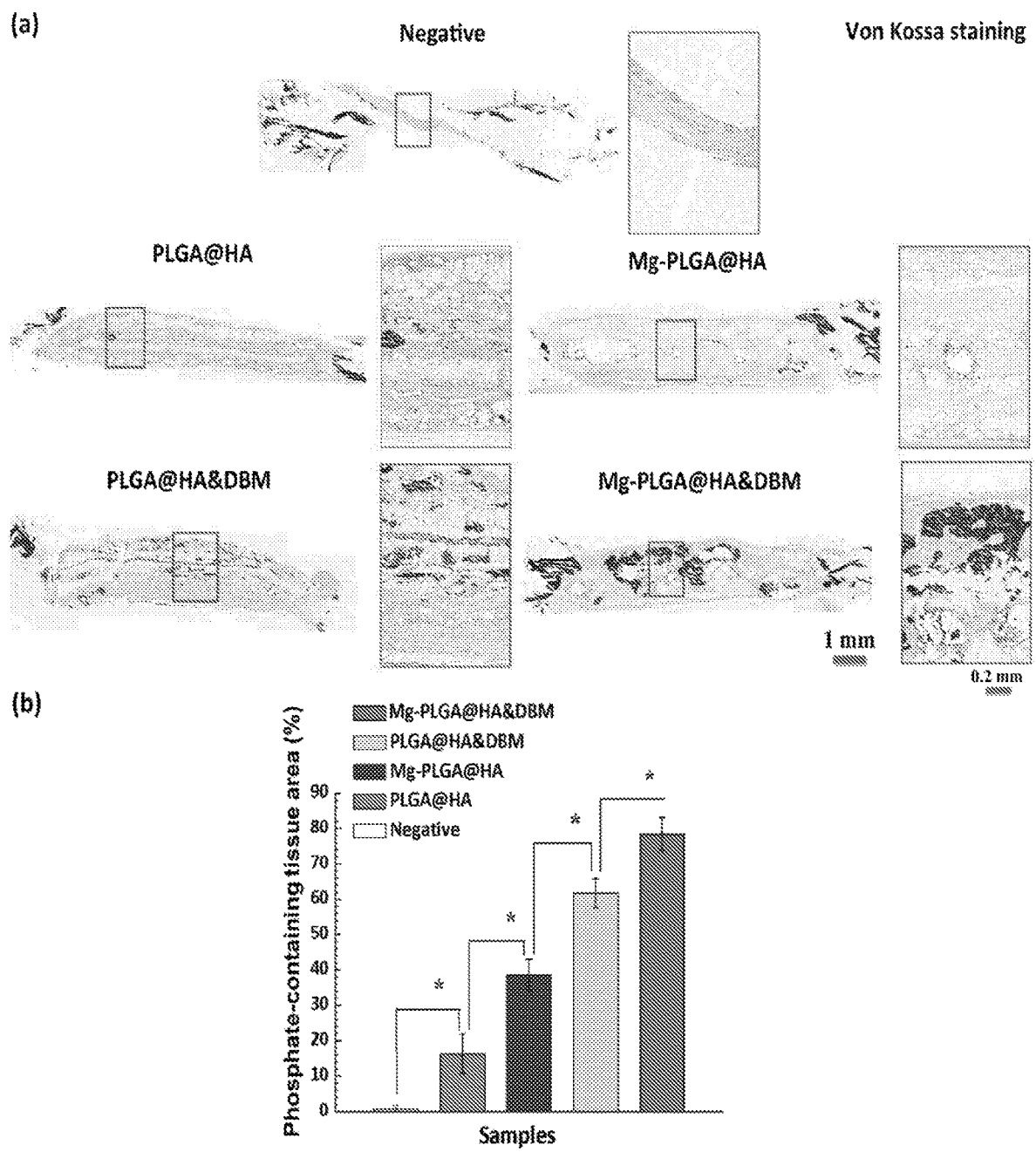
FIG. 4 shows view (a) which are images of Von Kossa staining of scaffolds after implantation in critical-sized calvarial defects for 12 weeks, and view (b) which is a plot of the quantification for calcified bone-like area of Mg-PLGA@HA&DBM, PLGA@HA&DBM, Mg-PLGA@HA, PLGA@HA scaffolds and Negative controls after 12 weeks of implantation, in accordance with certain embodiments of the invention.

The Mg alloy mesh utilized in the reported composite scaffold provided critical mechanical properties and served to improve the in vitro osteogenic activity. The open mesh structure facilitated integration of the polymer and DBM with the structural elements and provided for tissue integration around the Mg alloy elements. As expected, the flexural stress and modulus of the PLGA@HA&DBM scaffold were significantly increased with inclusion of the mesh. With both DBM and the Mg mesh present, in vitro osteo-promotive effect (FIG. 2) and in vivo bone regeneration were also improved. Though no specific, isolated biological agents inducing osteogenic differentiation, such as plasmid DNA, PDGF, or BMP-2, were added, DBM has been shown to retain some BMP proteins and collagens. For prior studies in the rat model with DBM inclusion, correlations between osteogenic gene expression and ALP/calcium deposition have shown, specifically that DBM was associated with osteogenic gene expression, including COL1A1, ALP, OCN and ONN. The BMSC proliferative ability also appeared to be stronger with both DBM and Mg present, as evidenced by qualitative SEM images of cells on the scaffolds. Supporting this finding were results from an MTT metabolic activity assay. In observing the histological images from the rat implants, it is notable how new bone appeared to be regenerating preferentially in the vicinity of the Mg mesh struts. This was seen in the trichrome (FIGS. 3a and 3b), H&E (FIG. 3c), and von Kossa staining (FIG. 4). Further confirmation of this effect was found in the micro-computed tomography images where solid areas were visible along the Mg struts in Mg-PLGA@HA and Mg-PLGA@HA&DBM scaffolds, providing an outline of the originally implanted Mg mesh. This may be attributed to the Mg ions released by corrosion of magnesium promoting in vivo osteogenesis. In accordance with the invention, the examples provided metallic Mg-based alloy incorporated in a bone scaffold for calvarial bone defect repair.

Currently, a variety of biodegradable polymeric scaffolds, having different porous morphologies created using different methods, have been employed to repair critical-sized calvarial bone defects. The most commonly utilized biodegradable polymers include PLGA, poly (L-lactic acid) (PLLA), poly (ε-caprolactone) (PCL), and copolymers with these common polyesters. One of the effective strategies to improve the in vitro and in vivo osteogenesis of polymeric scaffolds has been the incorporation of bioactive reagents for controlled delivery to the defect region. Most commonly, bone morphogenetic proteins (BMPs, and BMP-2 in particular) and peptide derivates have shown effective bone regeneration. However, there have been morbidities associated with the release of BMP-2 in some clinical applications that include postoperative inflammation, ectopic bone formation, osteolysis and subsidence, and others. Relatively high concentrations of BMP-2 in the scaffold may be an issue for the placement of such devices in some locations and in some patient populations.

DBM, as a bioactive alternative, provides an array of biologically active molecules, including BMP-2 and a variety of other growth factors at more physiologic concentrations, as well as collagens and other extracellular matrix components to promote osteoconduction and osteoinduction. The material, however, presents some challenges associated with handling, stability after surgery, and identification of an appropriate carrier. A common difficulty in comparing DBM evaluation studies is the variability introduced based on the source of DBM and the effect of donor and processing methodology on the level of retained bioactivity. In the examples, a commercial canine source of DBM was utilized that had been shown to have efficacy in the canine model. While, the use of xenogenic material in the rat model may have reduced activity compared to an allogenic source, other experience has shown the use of xenogenic DBM to have a positive effect.

The PLGA@HA&DBM scaffold in the examples appeared to have a better bone regenerative efficacy in the rat critical sized calvarial defect. This may be attributable to the porous structure of this scaffold, the osteogenic efficacy of canine DBM or possibly the DBM loading strategy that benefit to the release of bioactive agents. Commonly used strategies to improve the osteogenic efficacy of DBM have been to incorporate additional bioactive reagents, which include BMP2, the stromal vascular fraction (SVF) cells and others. Comparing to DBM that has been combined with BMP2, Mg alloy mesh reinforced PLGA/DBM scaffold in the examples had a lower osteogenic efficacy, which can be attributed to the recognized osteogenic efficacy of BMP2. In addition, DBM combined with polymer in some cases has a slower bone regeneration rate compared with DBM alone, which may be due to the acidic degradation products of the polymer component aggravating local inflammatory reactions.

In the examples, PLGA was utilized as a secondary structural component, and was selected for its common application in a variety of approved medical devices. The PLGA provided a three-dimensional porous structure that could facilitate nutrient transfer, as well as provide a reservoir to hold the DBM and HA mixture. The in vivo results showed that bone regenerative efficacy of Mg alloy mesh reinforced PLGA/DBM scaffold was not at the level achievable by BMP-supplemented matrices. One would expect BMP provision to improve the results, but as noted above, there is interest in developing scaffolding materials that avoid such exogenous factor incorporation. However, other factors may have limited the bone regeneration response, including the slower degradation rate of higher molecular weight PLGA that may have occupied space, discouraging bone tissue ingrowth. The combination of PLGA and Mg alloy mesh might be expected to moderate the side effects from acidic degradation products of PLGA because of the alkaline corrosion products of Mg. The acidic environment generated from the PLGA degradation could accelerate both corrosion of Mg and degradation of PLGA, however the mild alkaline surroundings of the Mg alloy degradation might slow these degradation processes. The concurrent electrospinning and electrospray method used in the examples resulted in the porous structure of the scaffold and facile loading and delivery of DBM. The rotating target holding the Mg mesh ensured the Mg mesh was encapsulated by the PLGA fibers, as well as DBM particles being distributed into the scaffold. The loading strategy of DBM into composite materials may have an effect on the delivery and release of its bioactive components and thus the resulting bone regenerative efficacy. In the examples, viscous hyaluronic acid (HA) was used to suspend DBM particles, which made the electrospraying process easier to accomplish. The concentration of hyaluronic acid to suspend DBM particles was optimized to a range where higher or lower concentrations would not be suitable for electrospraying or DBM particle suspension.

As seen from the in vivo results, complete defect filling with regenerated calcified tissue was not achieved. Similar models in the art have demonstrated complete or near complete defect filling, however, as noted above, most of these models relied upon controlled growth factor release (e.g. BMP-2). Since the incorporation and release of exogenous growth factors have been associated with complications in some application areas and add substantial cost to a product, the avoidance of such a design feature has merit. Furthermore, an 8-mm diameter defect size was chosen as a critical-sized calvarial defect, which is considered as one of the most aggressive sizes for a rat. Since the primary target design was a mechanically reinforced hybrid scaffold with the biodegradable Mg mesh, it was considered that the mechanically strengthened scaffold may have further potential to heal larger sized defects requiring such mechanical support at the initial stage, as well as receiving potential osteo-promotive activity from the released Mg ions. Another limitation in the examples is that only one time point was evaluated and a later point may have yielded further calcified tissue elaboration, although a faster healing response would be desirable clinically. The calvarial defect regenerative degree experienced with the scaffolds after 4 and 8 week-implantation periods was observed using nondestructive micro-CT testing, however, no extensive bone regeneration was observed at those time points. It is notable that some of the polymer appeared macroscopically and in tissue sections to remain at the defect site. Since the polymer was not of primary importance structurally and principally served as a space filler and to carry the DBM, a faster degrading polymer system would be of interest to facilitate earlier tissue ingrowth.

Conclusions

A Mg mesh reinforced polymer/ECM (PLGA/DBM) hybrid scaffold was successfully fabricated by a concurrent method of electrospinning of PLGA solution and electrospray of DBM suspending in hyaluronic acid solution. The hybrid scaffold characterization results revealed that: (1) Mg alloy mesh was encapsulated by PLGA fibers, and (2) DBM particles were distributed in this scaffold. The flexural stress and modulus of PLGA/DBM hybrid scaffold was significantly improved by the reinforced Mg alloy mesh. The Mg mesh reinforced PLGA/DBM hybrid scaffold promoted in vitro osteogenic differentiation of BMSCs as well stimulated bone regeneration in rat calvarial defects as compared to the other control scaffolds. The combination of DBM and Mg alloy mesh in this hybrid scaffold showed a combined beneficial effect in vitro and in a critical-sized bone defect model. These results suggest that this Mg alloy mesh reinforced polymer/extracellular matrix hybrid scaffold according to the invention is suitable for use in the critical-sized bone regeneration where supplementation with exogenous growth factor is not employed.

The invention claimed is:

1. A biomimetic, biodegradable scaffold, comprising:
a polymer/demineralized bone matrix composite, the composite comprising:
polymer fibers selected from the group consisting of nanofibers, microfibers, and combinations thereof, comprising poly(lactic-co-glycolic acid); and
an extracellular demineralized bone matrix derived from a precursor solution comprising demineralized bone matrix suspended in hyaluronic acid, applied to the polymer fibers; and
a mesh substrate comprising an etched magnesium alloy foil, embedded in the composite or encapsulated by the composite and effective to release Mg ions to stimulate bone regeneration,
wherein the composite is a porous and an interconnected fiber structure,
wherein the scaffold stimulates bone tissue regeneration for calvarial critical sized defects, absent of an exogenous growth factor, and
wherein the scaffold has a flexural modulus of greater than 500 MPa to at least 560 MPa.

2. The scaffold of claim 1, wherein the scaffold comprises collagen selected from type I, type IV, type X and mixtures thereof.

3. The scaffold of claim 1, wherein the scaffold comprises growth factor BMP.

* * * * *